(12) United States Patent
Kipke et al.

(10) Patent No.: US 6,820,506 B2
(45) Date of Patent: Nov. 23, 2004

(54) MULTI-CHAMBERED PUMP-VALVE DEVICE

(75) Inventors: Cary A. Kipke, Woodbury, MN (US); Jeffrey C. Pederson, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 143 days.

(21) Appl. No.: 10/107,622

(22) Filed: Mar. 27, 2002

(65) Prior Publication Data

US 2003/0183020 A1 Oct. 2, 2003

(51) Int. Cl.[7] .................................................. G01N 1/00
(52) U.S. Cl. ...................................... 73/863; 73/864.35
(58) Field of Search .............................. 73/64.56, 61.63, 73/863.23, 863.01, 863, 864.35; 422/63, 82.01–82.11, 81; 436/43, 150; 210/416.1, 418, 420, 422

(56) References Cited

U.S. PATENT DOCUMENTS

| | | | |
|---|---|---|---|
| 3,493,503 A | | 2/1970 | Mass |
| 4,138,474 A | | 2/1979 | Updike |
| 4,840,730 A | | 6/1989 | Saxena |
| 4,889,692 A | * | 12/1989 | Holtzman ................... 422/102 |
| 4,892,710 A | | 1/1990 | Wong et al. |
| 4,908,187 A | * | 3/1990 | Holmquist et al. ........... 422/81 |
| 5,133,869 A | * | 7/1992 | Taniguchi et al. .......... 210/656 |
| 5,330,916 A | | 7/1994 | Williams et al. |
| 5,786,182 A | | 7/1998 | Catanzariti et al. |
| 5,885,789 A | * | 3/1999 | Kardos et al. ................. 435/28 |
| 5,895,764 A | * | 4/1999 | Sklar et al. .................... 436/63 |
| 5,935,437 A | * | 8/1999 | Whitmore |
| 6,019,897 A | | 2/2000 | Horsman et al. |
| 6,048,457 A | | 4/2000 | Kopaciewicz et al. |
| 6,348,354 B1 | * | 2/2002 | Adolfsen et al. |
| 6,350,987 B1 | * | 2/2002 | Northrup et al. ........... 250/282 |
| 6,395,229 B1 | | 5/2002 | Markelov |

FOREIGN PATENT DOCUMENTS

| | | |
|---|---|---|
| WO | WO 01/19484 A1 | 3/2001 |
| WO | WO 01/42487 A2 | 6/2001 |

* cited by examiner

Primary Examiner—Robert Raevis
(74) Attorney, Agent, or Firm—Christopher D. Gram; Robert W. Sprague

(57) ABSTRACT

A multi-chambered pump-valve device for performing chemical processes, detections or analyses is described herein. The device includes a plurality of chambers having variable volumes in fluid communication with one another via one or more passageways. Liquid may be directed through the device by merely changing the volumes of two or more chambers. Despite the simplicity of the mode for transferring liquids in the device, complex chemical processing sequences may be performed using the device. A plurality of devices may be incorporated into a larger apparatus so that a plurality of chemical processing operations may be performed substantially simultaneously in parallel.

21 Claims, 6 Drawing Sheets

MULTI-CHAMBERED PUMP-VALVE DEVICE

BACKGROUND OF THE INVENTION

Modern chemical (including biochemical) practice includes numerous techniques for treating a liquid sample: mixing, reacting, filtering, dialyzing, synthesizing, fractionating, detecting, catalyzing (including enzymatically catalyzing) reactions, performing various separations, and the like.

For example, it may be desirable to remove solvent from a liquid sample in order to concentrate one or more solutes so that they may be analyzed, detected, further treated, etc. It also may be desirable to remove solutes, including macromolecular solutes or low molecular weight ions, each of which may interfere with analysis, detection or further treatment of one or more solutes of interest. This may be particularly so in biochemical practice, where complex mixtures of biological molecules can be obtained from living organisms, especially when the presence of a particular chemical species may interfere with the detection, analysis or further treatment of other solutes in the mixture.

Standard chromatographic techniques may be useful for performing many types of chemical separations. In addition, modified chromatographic methods in which a sorptive or reactive medium is cast in-place in a structure such as a pipette tip may be used to perform chemical separations on microliter-volume samples. In contrast to standard chromatographic methods, such modified, microliter-volume chromatographic methods can include a device that permits a sample to be subjected to multiple passes through the sorptive or reactive medium, thereby allowing multiple opportunities for the chemical separation to progress so long as the sample does not saturate the sorptive or reactive capacity of the medium. However, such devices may not be convenient for chemical separations in samples of larger volumes, e.g., milliliter or multiple-milliliter volumes.

Certain chromatography systems include a plurality of pumps to supply solvent to a plurality of chromatography columns. Each pump includes a chamber with a movable piston, an inflow valve and an outflow valve. Withdrawing the pistons from the chambers generates a vacuum in each chamber that draws solvent through the inflow valve and into the chamber. When the desired delivery volume of solvent has been drawn into each chamber, the pistons may be pushed back into the chambers, thereby forcing the solvent through the outflow valve and into the chromatography column. The pistons may be driven in concert using a pneumatic or hydraulic system.

Some devices designed for continuous chromatography have been adapted to be useful for the purpose of treating a liquid sample by depleting one or more undesirable chemical species. In such adaptations, the chromatography column is replaced by an element containing a substance selected to perform the desired depletion treatment, such as a functionalized solid support. The samples requiring treatment may be introduced into the buffer stream, thereby allowing the chemical species that are to be depleted from the sample to interact with the depletion element. Such devices may have at least two reservoirs, one for carrying the liquid sample, and a second for generating the column. In such devices, a second buffer can be used to elute the separated species from the depletion element so that the depletion element may be used to treat one or more subsequent samples.

Alternatively, certain batch processes are known for depleting an undesirable chemical species from a liquid sample. In such processes, a small chamber may include an article that contains a depletion substance selected to perform the desired depletion, i.e., removal of at least a portion of an undesirable chemical species from the liquid sample. A sample may be flushed through the chamber using, for example, low speed centrifugation or syringe plunger pressure, thereby allowing the depletion substance to remove the undesirable chemical species from the sample. For complete depletion, it may be necessary to pass the sample through the depletion substance more than once, thus requiring the operator to collect the partially depleted sample and recycle it through the process.

Certain other devices are designed for extraction of nucleic acids from a sample without pipetting. The sample and a lysis buffer are predispensed in vessels such as syringes that are interconnected through a narrow passage. The sample and lysis buffer can be mixed by transferring the sample and buffer mixture back and forth from one vessel to the other. One of the vessels can contain, for example, an extraction matrix for extracting nucleic acids from the sample and buffer mixture. Repeated transfer of the mixture ensures thorough mixing and offers multiple opportunities for nucleic acids to be extracted from the mixture by the matrix.

The utility of many chromatography-based devices and procedures may be limited; such devices may not be suitable for performing chemical syntheses, high-throughput analyses, or processing sequences involving multiple buffers, solutions and/or reagent in an automated manner, and the separated chemical species may be eluted in relatively large volumes of elution buffer, necessitating a concentration step before the eluted chemical species may be used for subsequent analysis or further treatment.

Many standard procedures exist for detection and analysis of one or more particular chemical species in a liquid sample. In many cases, such processes require that the sample be subjected to certain preparatory steps prior to the actual detection or analytical steps. In some cases, the sample preparation may be labor-intensive. Also, in some cases, the sample preparation may be incompatible with the detection or analytical method, e.g., the pH of buffers used in sample preparation and the analytical method may be different and incompatible. In such cases, it may be necessary to manually adjust one or more chemical properties of the prepared sample (e.g., pH, concentration, etc.) prior to performing the desired detection or analytical test. Consequently, efficiency of the overall process may be reduced, even to the point that the devices and processes being used may become unsuited for high-throughput analysis of the samples.

Therefore, a need exists for a device that may be employed in order to subject a liquid sample to one or more of a broad range of chemical treatments. Furthermore, a need exists for such a device that may be automated or is otherwise suitable for use in high-throughput analyses.

SUMMARY OF THE INVENTION

The present invention provides a device that is highly versatile and may be used to subject a liquid sample to one or more of a wide variety of chemical processing operations. Various embodiments of a device according to the present invention may provide the ability to perform high-throughput chemical processing, multi-step chemical processing, analyte detections, sample preparation, chemical separations and the like, as well as combinations of two or more of any of the foregoing.

Thus, the present invention provides a device for treating a liquid sample including: a first chamber having a variable volume; a second chamber having a variable volume; a third chamber having a variable volume; an interconnect comprising one or more passageways, each passageway engaged with one or more chambers so that the interconnect provides fluid communication between the first chamber, second chamber and third chamber; and a treating substance included in at least one of the first chamber, the second chamber, the third chamber, or at least one passageway of the interconnect; wherein the device is configured so that movement of the liquid sample through the device is controlled by changing the variable volumes of two or more chambers.

In certain embodiments, syringes or bladders may provide the variable-volume chambers. The device may include additional elements such as one or more detection elements, temperature-regulation elements or actuators for regulating the volumes of one or more chambers. Such additional elements may be controlled by a controlling element such as a programmable microprocessor.

In another aspect, the present invention provides an apparatus for substantially simultaneously treating a plurality of liquid samples, the apparatus including: a plurality of units, each unit including a first chamber having a variable volume, a second chamber having a variable volume, a third chamber having a variable volume, an interconnect comprising one or more passageways, each passageway engaged with one or more chambers so that the interconnect provides fluid communication between the chambers, and a treating substance included in at least one of the first chamber, the second chamber, the third chamber or a portion of the interconnect; an actuator connected to two or more first chambers for regulating the plurality of first chamber volumes; an actuator connected to two or more second chambers for regulating the plurality of second chamber volumes; and an actuator connected to two or more third chambers for regulating the plurality of third chamber volumes.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1:
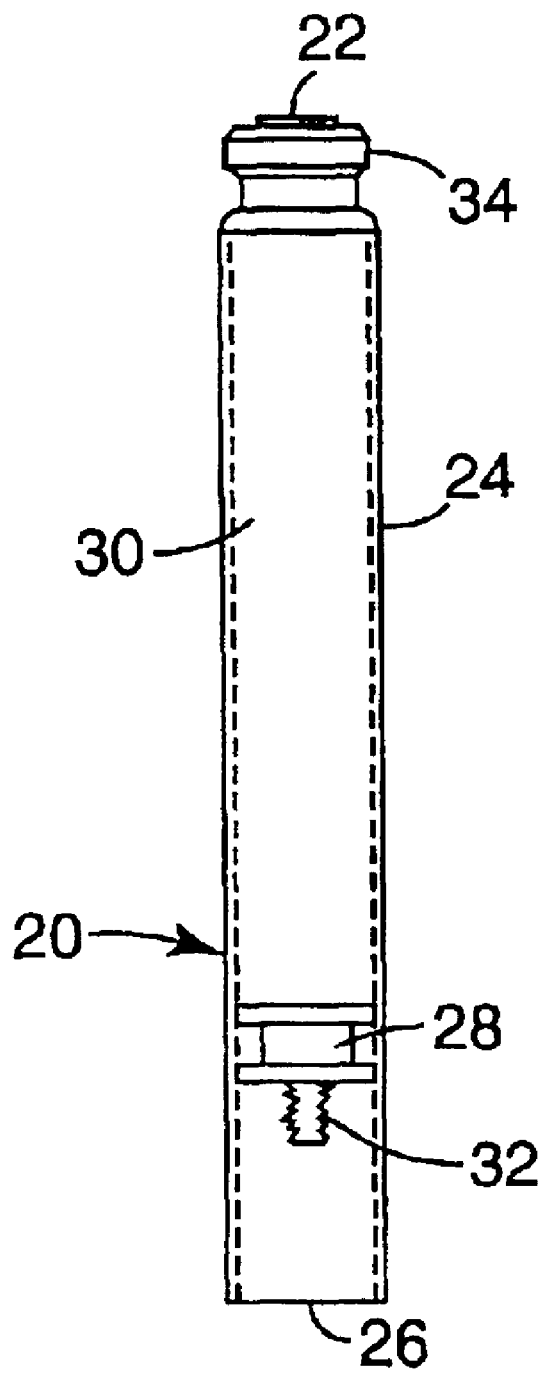
FIG. 1 is a plan view of a cartridge having a variable-volume chamber according to the present invention.

The fields of genomics and proteomics present challenges to modern chemical and biochemical processing systems. High-throughput, multi-step processing may be desirable for detection and/or analysis of nucleotides, in the case of genomics, or proteins, in the case of proteomics. In one aspect, the present invention provides a device suitable for performing a wide range of chemical processes on a liquid sample. As used herein, liquid sample may refer to an untreated liquid sample, such as a liquid sample as it is initially loaded into the device. Alternatively, the term liquid sample may include any partially-treated sample: either a) a sample that has been subjected to something less than an intended plurality of treatment steps in a multi-step treatment sequence, or b) that portion of a sample that has been treated if, for example, only a fraction of the total sample volume is subjected to a particular treatment while holding the remainder of the sample in either temporary or permanent reserve.

In another aspect, the present invention provides a system for performing multiple chemical processes on a liquid sample, such as multiple sample preparation process, detection process, analytical process, or any combination of two or more such processes. In yet another aspect, the present invention provides a system in which a plurality of liquid samples may be subjected to one or more chemical process to achieve high-throughput utility. The samples may be treated in parallel, substantially simultaneously, or both.

A device according to the present invention may be suitable for treating one or more liquid samples by performing one or more chemical processes on the one or more liquid samples. Suitable chemical processes include, but are not limited to, mixing, reacting, filtering, dialyzing, synthesizing, fractionating, detecting, catalyzing (including enzymatically catalyzing) reactions, performing various separations, and combinations thereof.

The device generally includes a plurality of chambers having variable volumes. As used herein, the term chamber may refer to any structural form at least partially defining an internal volume. When used in this way, the term chamber includes the structure, such as a syringe or a bladder, that at least partially defines the internal volume. Thus, another element of the device may be attached to a portion of a chamber. Chamber also may be used to refer to the variable internal volume of, for example, a syringe, bladder, cartridge, or the like.

In some embodiments of the device of the present invention, chambers may be reversibly removable from the device. Thus, sample may be more or less continuously supplied by replacing a used sample chamber, emptied to any desired extent, with a replacement sample chamber that has been filled to a desired extent while the replacement chamber was off-line.

Some embodiments of the present invention may include disposable elements such as disposable syringes as variable-volume chambers. Devices having such disposable variable-volume chambers may reduce the cost of performing a chemical processing sequence that can employ such inexpensive disposable elements.

The chambers are in fluid communication with one another through an interconnect that provide fluid communication between the chambers through one or more passageways. The interconnect may be constructed of any suitable material that can provide one or more conduits or passageways between the chambers. The interconnect may be constructed of inexpensive material that allows the interconnect to be disposable. Thus, in combination with disposable variable-volume chamber elements, the device of the present invention may include a series of modular, disposable elements that permit one to rapidly reconfigure the device to perform a different chemical process treatment.

The interconnect may include a single central bore through its center as a passageway. Alternatively, the interconnect may include a plurality of passageways. For example, an interconnect having two ends may include two distinct end-to-end passageways with the passageways in fluid communication at a first end, but being in fluid isolation from one another along their length and each passageway being in fluid communication with a different chamber at the second end. If a plurality of chambers are present, the interconnect may be branched or unbranched in order to provide any desired level of fluid communication between the plurality of chambers.

The versatility of the present invention is provided, in part, by selection of a treating substance. As used herein, a treating substance is any substance that promotes chemical processing of a liquid sample, e.g., by one or more of the chemical processes identified above. Suitable treating substances include, but are not limited to, reactants, buffers, filters, membranes, beads, size exclusion media, functionalized solid supports, catalysts (including enzymes), markers, affinity reagents, and combinations thereof. A treating substance may be provided in any suitable form. For example, a treating substance may be provided as a filler, occupying at least a portion of a lumen in a passageway or a chamber. Alternatively, certain treating substances may be provided as a coating on a surface of a passageway or chamber.

A treating substance may be located in any portion of the device that permits contact with at least a portion of the liquid sample, thereby providing the opportunity for the treating substance to perform the desired treatment. Suitable locations for the treating substance include, but are not limited to, any chamber, any portion of the interconnect, including one or more passageways, and any combination thereof.

Because the device includes a plurality of potential locations for placement of the treating substance, it may be possible to design a device that provides more than one treating substance. When two or more treating substances are provided, they may be co-localized within the device or, alternatively, provided at two or more locations within the device. In one embodiment, for example, a functionalized support is provided in the interconnect and an elution buffer is provided in one of the chambers. Thus, the device of the present invention may be designed to perform a plurality of chemical treatments on a single liquid sample.

In another example, one treating substance may be provided as a coating on the lumen surface of a passageway and a second treating substance may be provided as a filler, occupying a portion of the volume of the passageway. Alternatively, a passageway may be filled or coated with a mixture of two treating substances. Thus, a single sample may be treated by each of the two treating substances substantially simultaneously. In yet another example, a device having an interconnect with dual passageways may include different treating substances in each passageway. In this way, one can perform two different chemical treatments on a single sample. The two treatments may be performed in parallel, substantially simultaneously, or both.

In an embodiment of the present invention in which the interconnect comprises a plurality of passageways, as described above, each passageway may include a different treating substance than another of the plurality of passageways. For example, an interconnect having two distinct end-to-end passageways with the passageways in fluid communication at a first end, but otherwise being in fluid isolation from one another and in fluid communication with different chambers at the second end may include different treating substances in the two passageways. When used by moving liquid from the first end to the second end, such an interconnect may allow one to divide a sample and provide two different chemical treatments to the divided sample. When used by moving liquid from the second end to the first end, such an interconnect may allow one to combine two solutions, such as reagents, that have separately received different chemical treatments. Alternatively, the same treating substance may be provided in each passageway so that two solutions can be combined that have separately received similar chemical treatments. In other embodiments, the interconnect may include three or more passageways.

Another feature of the present invention, as will be explained in more detail below, is that a liquid, such as a sample, buffer, reactant, or wash solution, may be directed through the device through the coordinated control of the volumes of one or more chambers, so-called "passive valving." Thus, the flow of liquid may be directed through the device in a particularized sequence merely by controlling the volumes of selected chambers. In a device in which a plurality of treating substances has been provided, a sample may be subjected to multiple, sequential treatments by selectively directing liquid through the device in a desired sequence. A device according to the present invention may include one or more check valves or other mechanically or electronically controlled valves. However, passive valving is inexpensive and may prove less prone to failure.

Either the sample or the treating substance, if suitably liquid, may be the liquid directed through device in order to perform multiple chemical treatments. That is, if a treating substance is liquid, it may be directed to contact the sample at the appropriate time during the treatment process. Alternatively, the sample may be directed to contact the desired treating substance at the appropriate time during the treatment process. A multi-step treatment sequence may use any suitable combination of directing liquid sample, treating substances, mixtures thereof, or any combination of the foregoing in order to perform the desired chemical processing. In general, the versatility provided by the ability to control the flow of liquids through the device allows one to design and/or select any desired processing sequence.

Another feature of the present invention is that the device may include any number of chambers simultaneously connected to the interconnect. Thus, complex treatments that include multiple reactants, buffers, washes, and the like may be performed using the present invention, merely by designing the device to provide additional chambers that have been preloaded with materials desired for the complex treatment sequence. In this way, multi-step chemical processing sequences may be performed without having to remove and replace chambers in order to provide treating substances for subsequent steps in a multi-step processing sequence. This embodiment of the device of the present invention may be particularly suited to performing automated, high-throughput chemical process sequences such as those desirable for sample preparation for genomic or proteomic analyses.

In some embodiments, however, the chambers may be reversibly interchangeable in the device. That is, the device may include reversibly sealable ports, through which fluid communication between one chamber and the remainder of the device can be established. Thus, the contents of a chamber, e.g., a wash buffer, may be dispensed from the chamber into the remainder of the device to the desired extent. The used chamber may be removed and replaced with another chamber containing contents desired for a subsequent step in the process sequence, e.g., a reactant or another wash buffer.

A device according to the present invention also may include one or more additional elements selected to facilitate particular steps in a chemical treatment process. For example, a device may include one or more detection elements designed to detect at least a portion of a treated or untreated sample. Suitable detection elements include, but are not limited to, spectrophotometric detectors, fluorescence detectors, pH detectors, electrical conductivity detectors or refractive index detectors. Such detector elements may be integrally incorporated into the device or may be an element external to the device itself, but adapted for use with the device. Detector elements may be adapted to detect one or more chemical species in the interconnect or one or more chambers.

Another example of an additional element that may be used in connection with a device according to the present invention is a temperature-regulating element. Such an element may regulate the temperature in the interconnect or one or more chambers in order to at least partially control the progress of a particular step in a chemical processing sequence. For example, the kinetics of certain types of reactions or other chemical interactions may be controlled, at least in part, by controlling the temperature at which such steps are performed.

Additionally, actuators may be attached to the chambers for controlling the variable volumes of the chambers, as will be described in greater detail below.

Detection elements, temperature-regulating elements and actuators may be controlled by a controlling element, e.g., a programmable microprocessor. Controlling such elements with a controlling element such as a programmable microprocessor allows one to design complex sequences of chemical processing steps, load the desired samples, buffers, reactants and the like, activate the controlling element and have the sequence performed automatically, thereby reducing the manual cost of performing the chemical processing sequence.

The apparatus according to the present invention includes chambers having a variable volume. Variable-volume chambers may be provided in any suitable mechanical form including, but not limited to, a piston-like device such as a syringe, a container with a flexible wall such as a bladder, an enclosure having an elastic element such as a bellows, and a rolling diaphragm device. Some embodiments of the present invention can be constructed so that the variable-volume chambers are provided by commercially available disposable syringes. Alternatively, a variable-volume chamber may be provided by a cartridge having an open end and a chamber defined, in part, by a chamber wall. The cartridge can serve as a syringe when equipped with a moveable plug fitted to form a slidable fluid-tight seal with the chamber wall when the plug is inserted into the cartridge through the open end.

FIG. 1 shows a plan view of a cartridge 20 suitable for providing a variable-volume chamber in connection with the present invention. The cartridge 20 may include a cartridge body 24 that includes an open end 26 and a septum 22 at the end of the cartridge body 24 generally opposed to the open end 26. A movable plug 28 may be disposed within the cartridge 20, thereby at least partially defining the variable-volume chamber 30. In certain embodiments, the walls of the cartridge body 24 and the septum 22 may remain substantially stationary while the device is in use. In such embodiments, the variable nature of the variable-volume chamber 30 is substantially dependent upon position of the moveable plug 28 within the cartridge 20.

The movable plug 28 may include a releasable connection 32 such as threaded stud for convenient connection to means for controlling the position of the moveable plug 28 and, therefore, the volume of the variable-volume chamber 30. As just one example, a plunger rod may be connected to the moveable plug 28, thereby adapting the cartridge for manual or automated control of the position of the moveable plug 28. Any means for controlling the position of the moveable plug 28 may be suitable for use in the present invention, however.

The cartridge 20, when used to provide the variable-volume chamber, also may include a lubricant to facilitate movement of the movable plug 28 against the interior wall of the cartridge body 24. The lubricant may be an integral component of, or coated onto, at least a portion of the moveable plug 28, at least a portion of the cartridge body 24, or both. Suitable lubricants may be selected to be inert with respect to materials intended to be contained within the variable volume 30 of the cartridge 20. Suitable lubricants include, but are not limited to, silicones, silanes and hydrocarbons. In some embodiments, the septum 22 may be fixed to the cartridge body 24 by a cap such as an aluminum cap 34.

The present invention is hereafter described in terms of a device having variable-volume chambers provided by cartridges such as the cartridge illustrated in FIG. 1 and described above. However, other mechanical forms of providing a variable-volume chamber (such as a bladder, bellows, alternative forms of syringes, etc.) may be equally suitable for use in the present invention, unless otherwise specified.

Also, identification of particular chambers as intended for loading of a sample, reagent, buffer or the like, or for use as a collection chamber, is for convenience and illustrative purposes only. A feature of the device of the present invention is that the particular function of any one chamber may be determined, in part, by the treatment operation sequence being followed by the operator.

Figure 2A:
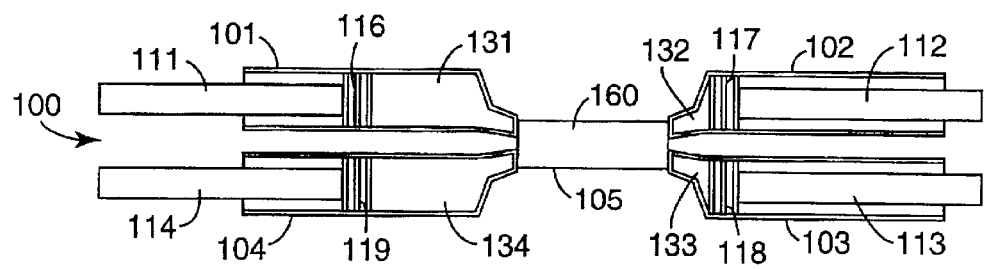
FIGS. 2A, 2B, and 2C are schematic drawings illustrating a single treatment operation sequence utilizing a device having four chambers.
Figure 2B:
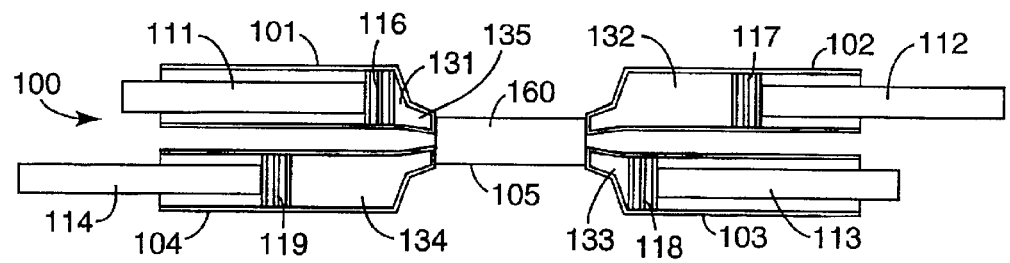
Figure 2C:
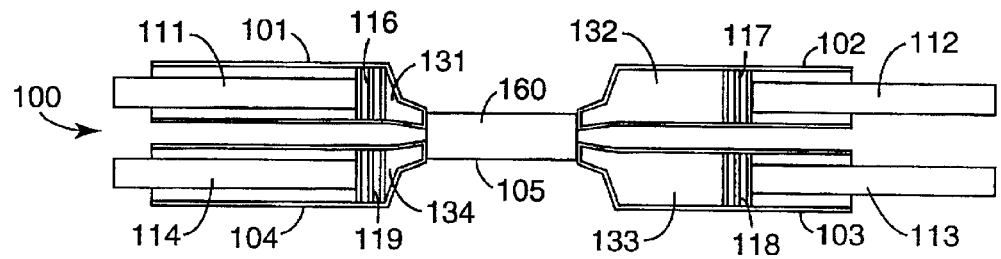

FIGS. 2A, 2B, and 2C provide a schematic illustration of one example of a treatment operation sequence using a device 100 that includes four cartridges 101, 102, 103 and 104, each cartridge serving as a chamber having a variable volume. Such a treatment operation sequence might be characterized as a single-pass sequence protocol because the liquid sample is contacted with a treating substance only once, i.e., in a single pass. An interconnect 105 provides fluid communication between the cartridges through an internal passageway (not shown). Each cartridge may be engaged with the interconnect 105 so that such fluid communication between the chambers is maintained.

As one example of the single-pass sequence protocol (FIG. 2A), the variable-volume chamber 131 of cartridge 101 may be filled with a liquid sample and, therefore, be designated the sample chamber. The variable-volume chamber 134 of cartridge 104 may be filled with a second solution, e.g., a wash buffer. Cartridge 102 and cartridge 103 can begin the protocol with their movable plugs 117 and 118, respectively, positioned forward as shown, thereby minimizing the volume of their respective chambers 132 and 133. The interconnect 105 may contain a treating substance 160 such as an immobilized molecule selected to interact with the liquid sample in a predetermined way, thereby providing chemical treatment of the liquid sample.

FIG. 2B illustrates the movement of the liquid sample during a single-pass protocol. The plunger rods of selected cartridges may be immobilized to prevent movement of liquid into the chambers of the selected cartridges (e.g., plunger rods 114 and 113 are immobilized in FIG. 2B). The plunger rod 111, shown connected to the moveable plug 116 in cartridge 101, may be advanced, thereby decreasing the volume of chamber 131. The plunger rod 111 may be completely advanced, as shown in FIG. 2B, or only partially advanced, as desired. The rate and degree of plunger rod advancement may be controlled manually or automatically.

As plunger rod 111 is advanced, the volume of chamber 131 is decreased, thereby forcing liquid sample out of chamber 131, into the interconnect 105 and into contact with the treating substance 160. At the same time, plunger rod 112 and moveable plug 117 are displaced outward with respect to cartridge 102, thereby increasing the volume of chamber 132. Thus, the portion of the liquid sample that has been passed through the interconnect 105 and, therefore, has been chemically treated by the treating substance 160, is directed toward chamber 132. Plunger rod 111 may be advanced until the desired amount of liquid sample has been directed through the treating substance 160.

The outward movement of plunger rod 112 may be passive, i.e., it may be pushed outward by the treated sample being directed toward chamber 132 as a result of decreasing the volume of chamber 131 while the plunger rods 113 and 114 remain immobilized. Alternatively, the outward movement of the plunger rod 112 may be active, i.e., the plunger rod 112 may be pulled outward. Such active outward movement of the plunger rod 112 may be controlled manually or automatically.

If desired, one or more of the variable-volume chambers may be designed to minimize any residual volume 135 that may exist when the moveable plug has been advanced completely. Such minimizing of the residual volume may increase the efficiency with which the liquid sample is used.

FIG. 2C illustrates a subsequent processing step executed after the liquid sample is dispensed from chamber 131 to the desired extent. The description that follows is provided in the context of the subsequent chemical processing step being a wash step. However, any suitable step in a chemical processing treatment operation sequence, e.g., an elution step, may be performed. Accordingly, any solution suitable for the desired chemical processing step may be provided in chamber 134.

For a wash step, a wash solution may be provided in the variable-volume chamber 134 of cartridge 104. The plunger rod 111 of cartridge 101 may be immobilized to prevent movement of liquid back into chamber 131. The plunger rod 114 and moveable plug 119 are advanced, thereby directing wash solution into the interconnect 105. As described above for the advancement of plunger rod 111, advancement of plunger rod 114, may be controlled manually or automatically. If plunger rod 113 remains immobilized and plunger rod 112 remains moveable while plunger rod 114 is advanced, then the wash solution entering the interconnect 105 from chamber 134 will direct additional treated sample into chamber 132.

When the desired amount of treated sample is collected in chamber 132, plunger rod 112 may be immobilized and plunger rod 113 may be released, thereby allowing plunger rod 113 to be outwardly displaced with respect to cartridge 103 and increasing the volume of chamber 133. Any subsequent advance of plunger rod 114 will cause treated sample, wash solution, or a mixture of both to be directed into chamber 133. The outward movement of the plunger rod 113 may be passive or active, as described above for the control of the outward movement of plunger rod 112.

As indicated above, the solution loaded in chamber 134 may provide one or more functions in addition to, or in lieu of, providing a wash. For example, the solution loaded into chamber 134 may, for example, regenerate the treating substance 160 for treatment of a subsequent sample, or release a component that has been removed from the liquid sample by, for example, adsorption to the treating substance 160. In the latter case, the component of the liquid sample released from the treating substance 160 may be collected in the solution that fills chamber 133. In the treatment operation sequence illustrated in FIGS. 2A, 2B and 2C, chamber 132 and chamber 133 contain processed solutions that have passed through interconnect 105, one or both of which may be useful for subsequent analysis, detection or further treatment.

Figure 3:
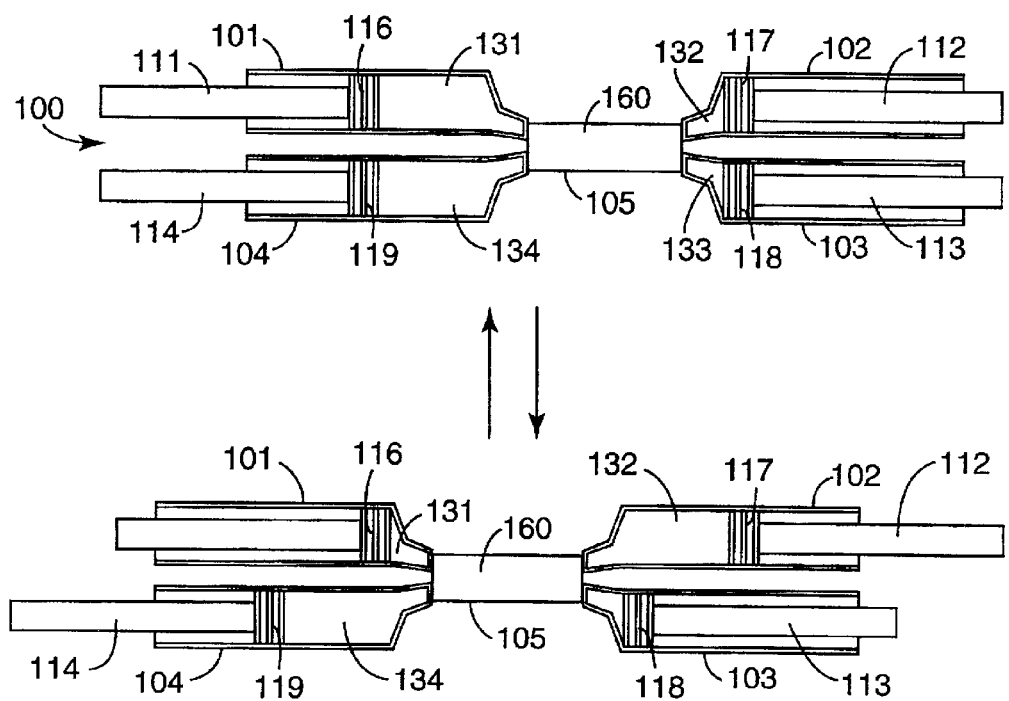
FIG. 3 is a schematic drawing illustrating an optional step that employs reversible flow.

FIG. 3 provides a schematic illustration of an optional feature of a treatment operation sequence such as that shown in FIGS. 2A, 2B and 2C. This optional feature allows the device to perform a multi-pass sequence protocol in which the liquid sample is contacted with the treating substance in multiple passes. FIG. 3 shows that the movement of the liquid between any two chambers may be reversible. The device is illustrated schematically in FIG. 3 as in FIGS. 2A and 2B. Movement of the liquid sample from chamber 131 to chamber 132 may be accomplished as described above in the single-pass sequence protocol. After the liquid sample has been directed toward chamber 132 to the desired extent, the solution flow may be reversed by directing flow from chamber 132, through the interconnect 105, and back toward chamber 131. The reversed flow may be accomplished by advancing the plunger rod 112 connected to the moveable plug 117 into cartridge 102 while immobilizing the plunger rods 113 and 114 of cartridges 103 and 104, respectively. Again, the advancement of plunger rod 112 may be controlled manually or actively. Furthermore, the outward movement of moveable plug 116 may be controlled passively or actively, either manually or automatically, as described above.

Reciprocating the flow between chambers 131 and 132 may provide certain advantages over a single pass through the interconnect 105 and treating substance 160. For example, a single pass sometimes may not be sufficient to treat the liquid sample to the desired extent. The cycle illustrated in FIG. 3 can be performed multiple times until the liquid sample has been treated to the desired extent.

Although illustrated and discussed with respect to chambers 131 and 132, flow between any two chambers may be reversed if desired for a particular treatment operation sequence. Also, treatment sequences may be designed that incorporate a plurality of such reversible-flow steps, if desired.

The treated sample may be collected in any suitable variable-volume chamber, e.g., chamber 132. In some embodiments, the treated sample may be the desired substance. In other embodiments, one or more additional treatments steps may be desired to obtain the desired substance. For example, as described above with regard to the single-pass sequence protocol illustrated in FIGS. 2A–2C, a subsequent processing step such as a wash step or an elution step may be performed in order to obtain the desired substance. In one such protocol, the solution loaded in chamber 134 may release one or more desired molecules from the treating substance 160 and be collected in a suitable variable-volume chamber, e.g., chamber 133.

More complex treatment operation sequences also may be performed using a device according to the present invention. For example, a sample may be filtered by passing the sample (single- or multi-pass) through a selective filtration membrane as a treating substance, e.g., in the interconnect, in one direction. The filtered material may be collected by directing a wash solution in the opposite direction. The filtrate, filtered material, or both may be collected for further treatment, analysis or detection.

Also, synthetic reactions may be performed using a device according to the present invention. Reactants may be provided in one or more chambers as gasses, solids or liquids. Reactants may be provided individually or combined with at least one other reactant, for example, in solution, in suspension, in an emulsion, and the like. Moreover, molecules may be synthesized using a multi-step syntheses by merely providing either sufficient numbers of chambers to provide all of the required reactants or replacing used chambers with chambers loaded for use in a subsequent step of the synthesis. Such a complex synthetic pathway may include one or more clean-up steps such as filtration or separation in order to separate reaction products. One or more temperature-regulating elements may be employed to control the temperature at one or more steps in the synthetic pathway.

As another example, a device according to the present invention may be used to fractionate a sample. If many fractions are desired, continuous fractionation may be accomplished using a plurality of reversibly removable chambers for collecting the fractions. For example, the sample may be fractionated continuously by alternating the flow of the sample between two collection points while sequentially filling, removing and replacing the collection chambers connected to the treatment unit at each collection point. In this way, the flow of sample may be controlled so that the flow can be diverted when a particular collection chamber is filled to the desired extent, thereby allowing fraction collection to continue while the filled collection chamber is removed and replaced with a new collection chamber.

Complex chemical sequences that incorporate one or more different kinds of processes such as those described above may be performed using a device according to the present invention. Furthermore, because such a device may be controlled by a controlling element, such as a programmable microprocessor, such complex sequences may be performed under automated control, if desired.

Figure 4:
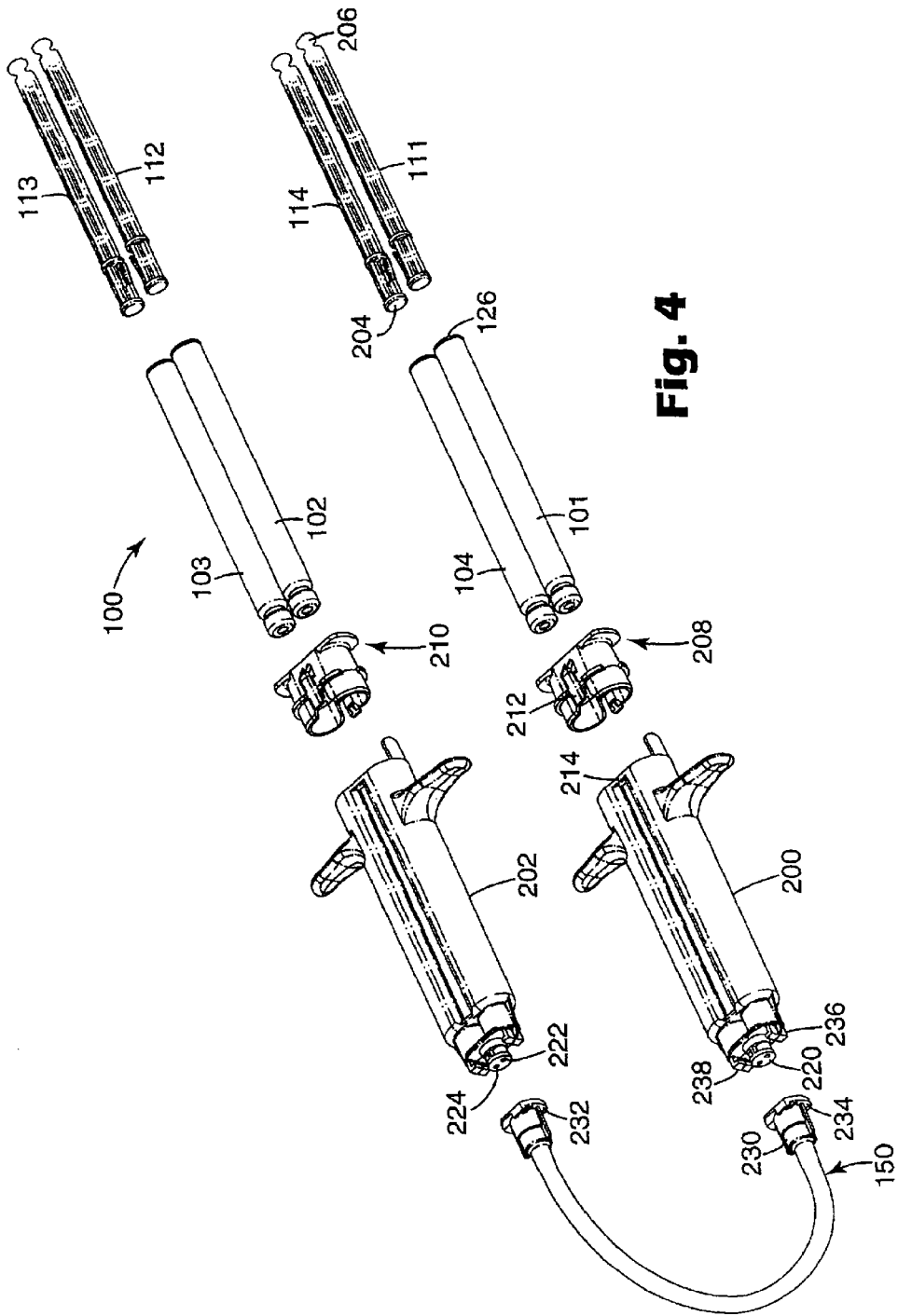
FIG. 4 is a perspective view of one embodiment of a device according to the present invention.

FIG. 4 provides a perspective exploded view of one embodiment of a device 100 suitable for carrying out the processes just described. The illustrated embodiment of the device 100 includes a plurality of variable-volume chambers, provided by four cartridges 101, 102, 103 and 104 and four plunger rods 111, 112, 113 and 114. An interconnect 105 provides fluid communication between the variable-volume chambers. In this example the interconnect 105 is in the shape of a "U" so that all of the plunger rods may be controlled from one side of the device. The "U"-shaped interconnect 105 permits one to easily control the position of plunger rods and, therefore, the volume of chambers on opposite sides of the interconnect because the ends of plunger rods controlling the volumes of the opposed chambers may be positioned side-by-side. This may be particularly advantageous if the plunger rods are being controlled manually because the operator can control the volumes of opposed chambers without reaching across the length of the device.

Figure 5:
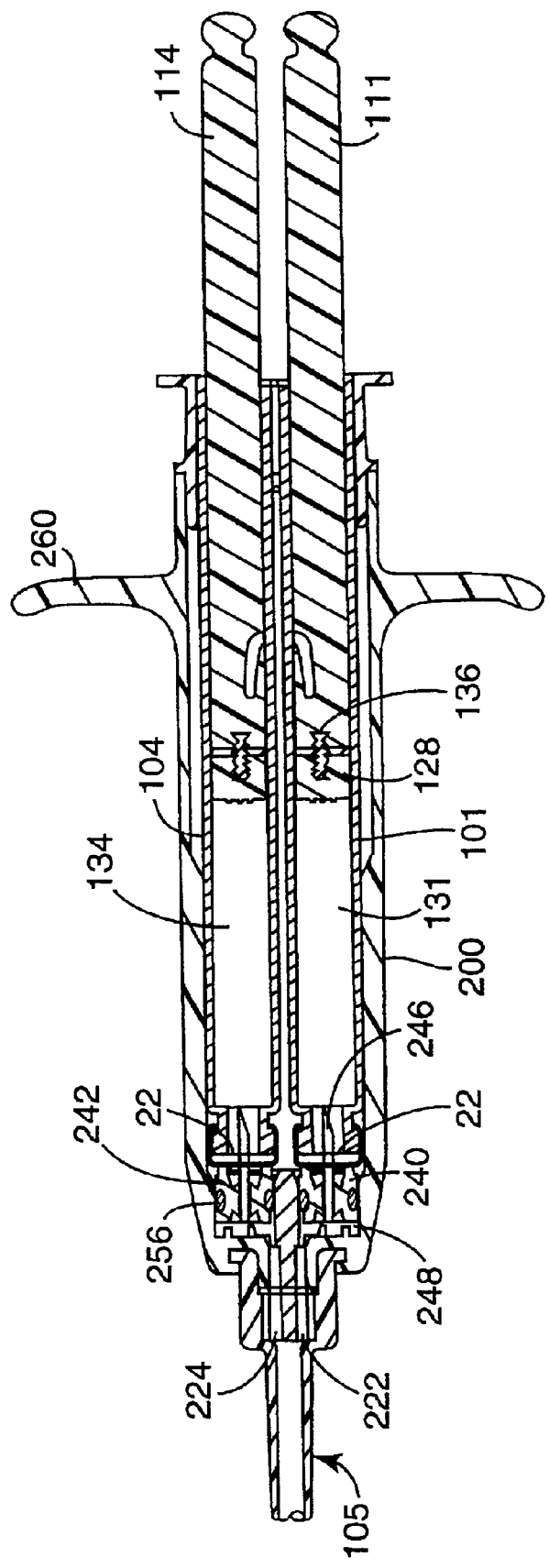
FIG. 5 is a plan cross-section view of a portion of the device depicted in FIG. 4.

Cartridges 101 and 104 may be designed to fit within a housing 200 while cartridges 102 and 103 may be designed to fit within a second housing 202. Plunger rods 111, 112, 113 and 114 may be sized and configured to be received in the open ends 126 of cartridges 101, 102, 103 and 104, respectively. Each plunger rod may be equipped at one end with threads 204 adapted to receive a thread stud 136 anchored in a movable plug 128, as shown in FIG. 5. Each plunger rod also may have an end 206 adapted to engage an automatic control device that will be described in more detail below. Alternatively, if the device designed to be operated under manual control, then thumb plates may be provided on the end of each plunger rod.

The device 100, as depicted in FIG. 4, may include retainers 208 and 210 that may serve to protect and support the cartridges, particularly when the cartridges may be susceptible to damage, such as when constructed from glass or when the cartridges are sufficiently longer than the housings 200 and 202 that additional support may be desirable. The retainers 208 and 210, when present, may be sized and shaped to receive one or more cartridges. The retainers 208 and 210 may include attachment means for releasably engaging the housings 200 and 202, respectively. In one embodiment, the attachment means are manually releasable and may reattach the retainers to the housings. The retainers may, for example, connect to the housings by a press fit or, alternatively, have an extending arm 212 that latches over a lip 214 near the proximal end of the housing 200.

Each of the housings 200 and 202 may include a nozzle 220. In embodiments in which the housing can accommodate a plurality of cartridges, the nozzle 220 may include a plurality of openings. For example, the embodiment illustrated in FIG. 4 includes a housing that can accommodate two cartridges and a nozzle 220 that has two openings 222 and 224. This may be seen with more particularity in connection with the embodiment illustrated in FIG. 5; opening 222 leads to chamber 131 and opening 224 leads to chamber 134.

The interconnect 105 may include a first end adapter 230 and a second end adapter 232, each configured to engage the nozzle end of the housing. In one embodiment, each of the end adapters 230 and 232 includes a base flange 234 adapted to engage complementary grips 236 and 238 adjacent to nozzle 220. However, any means for providing a fluid-tight seal between the interconnect 105 and the chambers may be suitable.

FIG. 5 provides a cross-section plan view of a portion of one embodiment of the device 100 according to the present invention. In this embodiment, the housing 200 includes a pair of piercers 240, each piercer configured to penetrate a septum 22 of a cartridge, thereby providing fluid communication between the chamber within each cartridge and the corresponding opening (222 or 224) of the nozzle. Each of the piercers 240 includes a hollow needle 246 anchored in a piercer body 242. The hollow needle 246 provides fluid communication between the chamber of a cartridge and a plenum 248. Therefore, for example, chamber 131 is in fluid communication with the interconnect 105 via needle 246, plenum 248 and opening 222. An O-ring 256 may be seated around the piercer bodies 242 to provide a fluid-tight seal for plenum 248. A finger flange 260 may be provided to facilitate manual actuation of the device.

Figure 6:
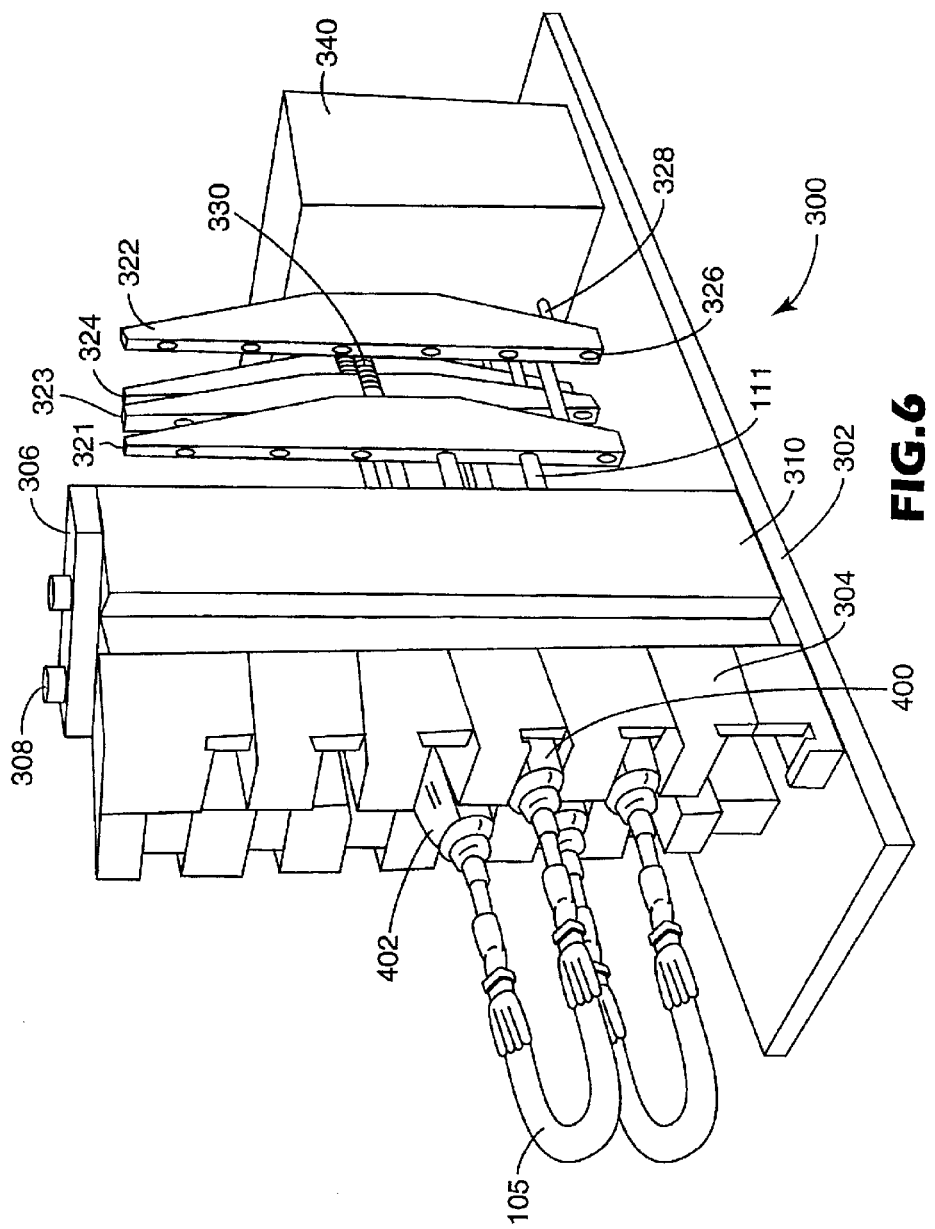
FIG. 6 is a perspective view of one embodiment of an apparatus for supporting and actuating multiple treatment units.

A device according to the present invention may be designed to stand alone. Alternatively, multiple devices may be incorporated as treatment units 400 in a larger apparatus 300, as shown in FIG. 6. The apparatus 300 may be designed for supporting and actuating multiple treatment units 400, thereby allowing chemical processing of multiple liquid samples in a single apparatus 300 to be performed in parallel. The apparatus 300 may be further designed to permit the chemical processing of multiple samples to be performed substantially simultaneously. The apparatus depicted in FIG. 6 provides for six treatment units 400 to be supported and actuated, but an apparatus 300 may be designed to accommodate any desired number of treatment units 400.

Housing support blocks 304 may be stacked on a base 302. The housings support blocks 304 may have recesses formed therein that are shaped so that each block can receive and support securely one or more treatment units 400. The support blocks 304 may be constructed of any suitable supportive medium including, but not limited to, polystyrene, polytetrafluoroethylene, polycarbonate, polypropylene and the like. The recesses may be formed by any process suitable for the particular material used to form the support blocks 304. For example, the recesses may be molded or milled into the support blocks 304.

If present, detection elements or temperature-regulating elements may be incorporated into or attached to the support blocks 304.

During operation of the apparatus 300, the support blocks 304 may be secured by any suitable means, e.g., a capture plate 306, as shown in FIG. 6, which may be bolted to one or more structural members 310 with bolts 308.

In certain embodiments, multiple treatment units 400 may be supported within a rack of support blocks 304 such that the treatment units 400 may be easily and quickly engaged or disengaged from the rack. Also, the treatment units 400 may be designed so that the element having the variable volume chamber, e.g., a syringe or bladder, may be easily and quickly engaged or disengaged from the treatment unit 400. Alternatively, the rack of support blocks may be easily and quickly engaged or disengaged from the base 302.

Embodiments in which at least a portion of the apparatus 300 may be easily and quickly engaged or disengaged may be particularly useful for certain applications. For example, such designs may permit one to collect fractions of a treated sample in separate chambers, e.g., syringes, and insert replacement collection chambers into the apparatus 300 for continuous, uninterrupted collection of treated sample.

In some embodiments of the apparatus of the present invention, a plurality of actuators may be present. The actuators, when present, may be designed for control of plunger rods associated with the treatment units. The actuators may be configured to provide any desired level of coordinated control of the plunger rods of one or more treatment units. Such coordinated control of plunger rods from multiple treatment units permits one to control the movement of liquid within multiple treatment units simply by controlling a single actuator. Thus, one may control the progress of multiple chemical processing sequences substantially simultaneously.

The embodiment depicted in FIG. 6 includes four actuators 321, 322, 323 and 324, each actuator designed to control the volumes of analogous chambers in each treatment unit housed within the apparatus. Because each treatment unit may include any number of variable volume chambers and each variable volume chamber may or may not be connected to an actuator, an apparatus 300 according to the present invention may include any number of actuators.

If coordinated control of chemical processing of multiple samples in parallel is desired, each actuator may be adapted to engage analogous plunger rods of each treatment unit. For example, actuator 321 may be engaged with the plunger rod 111 of the sample chamber of each treatment unit, the actuator 322 may be engaged with the plunger rod of a first collection chamber of each device, and so on. As shown in FIG. 6, each actuator may include multiple receptacles 326 for releasably connecting to plunger rods. The receptacles 326 may include quick release fastener complementary to a fastening structure on the plunger rod, e.g., a button end 206.

Each actuator is reversibly slidable, thereby capable of controlling the movement and location of each plunger rod attached to the actuator. Because the location of the moveable plug, which is attached to the plunger rod, at least partially determines the volume of the variable volume chamber that at least in part directs the flow of liquid within the treatment unit, the actuators may be used for parallel control the movement of liquid in each of a plurality of treatment units.

During the reversible sliding motion, the actuators may be supported by slide rods 328 and driven by, for example, lead screws 330. Other methods of creating controlled linear motion are possible. The lead screws 330 may be driven by motor-turned gears within a drive unit 340. Drive unit 340 also may include a control mechanism for the timing of the various motions that are needed for the different procedures, thereby providing automated control of the chemical processing sequence being performed in each treatment unit 400 of the apparatus 300. Such automated control may be particularly useful for performing high-throughput processing sequences such as sample preparation for genomic or proteomic analyses. The control mechanism may include a microprocessor, although alternative control mechanisms, such as cam followers or relay controllers, may be suitable.

Each actuator may be connected to the control mechanism so that the control mechanism can control the movement of each actuator. In this way, the volumes of the various chambers of each treatment unit 400 in the apparatus 300 are controlled by the control mechanism, thereby also controlling the movement of liquids from one chamber in a treatment unit to other chambers within the same treatment unit. Also, because each actuator may be connected to multiple analogous plunger rods, controlling the position of multiple analogous moveable plugs and, therefore, the volumes of multiple analogous chambers, the control mechanism can control the parallel processing of multiple samples simultaneously.

For simplicity, various features of the present invention have been described in isolation. Such descriptions shall not be construed to limit the scope of the present invention. One of the features of the present invention is the versatility of design provided by the device and the broad variety of chemical treatments that may be performed according to the present invention. Thus, the features of certain particular embodiments may be combined with the features of other embodiments to obtain additional embodiments of the present invention.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

In each example, glass cartridges (80 mm length and 7 mm internal diameter available from Kimble, Vineland N.J.) were used to contain liquid solutions or solids, as appropriate. The glass cartridges each included an open end and a nubbed end generally opposed to the open end. The cartridges were silicone-treated (560 Medical Fluid available from Dow Corning, Midland, Mich.) according to the manufacturer's recommendation to provide a lubricated surface to facilitate plunger movement within the cartridges.

A moveable rubber plug (7 mm diameter) having a threaded metal post (available from Abbott, Abbott Park, Ill.) was inserted into the open end of each glass cartridge. Each threaded post was attached to a plunger so that the position of the plug could be externally controlled.

Some cartridges were loaded with a solution or solid, as appropriate. Solution or solid was introduced into an opening at the nubbed end of the cartridge. The rubber plug was advanced until the solution or solid was level with the opening at the nubbed end of the cartridge. The nubbed end of the cartridge was crimp-sealed using a rubber-lined aluminum septum cap (available from Wheaton Pharmatech, Salisbury, Md.).

Other cartridges were intended for collection of treated samples. Collection cartridges were assembled by advancing the plug to its most forward position in the cartridge. The nubbed end of the cartridge was sealed using a rubber-lined aluminum septum cap as described above.

In each of the following examples, a dual barrel syringe housing (described in applicants' copending International Publication No. WO 01/67961, filed Mar. 10, 2000) was fitted with two glass cartridges assembled as described above and attached to each end of a glass column, thereby forming a closed system having four syringe chambers (two on each side of the glass column). The glass column (100 mm length and 3 mm internal diameter, available from Omnifit, Cambridge, England) was either packed with packing materials or used empty as a fluid conduit. When filled with packing material the column was sealed with end fittings containing 25 µm frits (also available from Omnifit). Each end of the column was attached to a dual barrel syringe housing with Luer-lock fittings.

In each example, cartridges (containing reagents, washes, buffers or empty, as appropriate for the particular example) were loaded into the dual barrel syringe housings. Each syringe housing included an insert having two 16-gauge needles capable of piercing the rubber-lined septum caps of the glass cartridges to be fitted into the housing. Each needle provided a conduit between a cartridge and an opening in a nozzle of the syringe housing. Each needle and its associated nozzle opening provided fluid communication between a cartridge loaded in the housing and the column.

Fluid movement through the system was controlled by immobilizing plunger rods associated with cartridges that were neither sources nor destinations of the liquids being transferred in a particular step. Positive pressure was placed on the plunger rod of the cartridge or cartridges that contained liquid to be transferred at a particular time. The plunger rod of a collection cartridge, i.e., the destination of the liquids being transferred during a particular step, was passively allowed to slide within its cartridge, thereby allowing the volume of the chamber in the cartridge to increase in response to the positive pressure applied to the source cartridge plunger rod(s). Unless otherwise indicated, liquid was directed through the system at a rate of approximately 0.5 mL/min.

Example 1

Ionic Immobilization

The system described above was used to construct an ionic immobilization system that was used for each of two runs, a single-pass run and a multi-pass run. For each run, the glass column was packed with 4% beaded agarose with immobilized iminodiacetic acid (available from Pierce, Rockford, Ill., copper ion binding capacity >0.9 mg). The column was equilibrated with distilled and deionized water to remove sodium azide preservative. Copper sulfate was dissolved in distilled and deionized water to form a 165 mM solution. 1.5 mL of the solution was loaded into a first glass cartridge. 2.5 mL distilled and deionized water was loaded into a second glass cartridge.

The first and second cartridges were inserted into one dual barrel syringe housing. A third cartridge and fourth cartridge were inserted into another dual barrel syringe housing attached to the other end of the glass column. The third and fourth cartridges were empty when inserted into the housing.

In the single-pass run, positive pressure was applied to the plunger rod of the first cartridge, thereby introducing the copper sulfate solution into the glass column and contacting the copper sulfate solution with the beaded agarose packed therein. The plunger rods of the second and fourth cartridges were immobilized, but the plunger rod of the third cartridge was not immobilized. Thus, after contacting the beaded agarose, the treated sample was directed toward and collected in the chamber of the third cartridge. When the plunger rod of the first cartridge was fully advanced, all of the copper sulfate had been introduced into the column.

The column was washed by immobilizing the plunger rod of the first cartridge and applying positive pressure to the plunger rod of the second cartridge so that the distilled water loaded in the second cartridge was introduced into the column, thereby washing unbound copper ions from the column. Because the plunger rod of the third cartridge was not immobilized, unbound copper ions washed from the column were directed toward and collected in the third cartridge. Thus, all of the unbound copper ions were collected in the third cartridge.

In the multi-pass run, the plunger rods of the second and fourth cartridges were immobilized as at the beginning of the single-pass run described above. Positive pressure was alternately applied to the plunger rods of the first and third cartridges so that the copper sulfate solution was passed back and forth through the agarose-packed column nine times. Whenever positive pressure was being applied to the plunger rod of one of the first or third cartridges, the plunger rod of the other cartridge ("the passive cartridge") was allowed to be displaced outward with respect to the cartridge, thereby allowing the solution to temporarily collect in the passive cartridge.

After nine passes through the column, the solution was collected in the third cartridge. Thereafter, the column was washed as described in the single-pass run. Thus, all of the unbound copper ions were collected in the third cartridge.

Approximately 3.8 mL of treated liquid was collected in the third cartridge in each run. The amount of copper ion in the starting solution, collected in the single-pass run and collected in the multi-pass run were analyzed spectrocolorometrically at 650 nm. The starting solution in each run contained approximately 15.73 mg of copper ion, far in excess of the binding capacity of the column.

The collected solution from the single-pass run contained 15.70 mg copper ions, indicating that the column immobilized 0.03 mg of copper ion in the single-pass run. The collected solution from the multi-pass run contained 15.43 mg of copper ions, indicating that the column immobilized 1.3 mg of copper ion in the multi-pass run. Thus, the column bound copper ions to less than 3% of capacity using the single-pass protocol, but the column bound copper ions to substantial saturation using the multi-pass protocol.

Example 2

Affinity Immobilization

An affinity immobilization system was constructed and used for each of two runs, a single-pass run and a multi-pass run. The system was constructed as described in Example 1, with the following exceptions: the glass column was packed with Mimetic Blue SA P6XL beads (available from ProMetric BioSciences Ltd., Isles of Man, British Isles) and was equilibrated with 25 mM sodium phosphate buffer, pH 5.5; 2.0 mL of human serum albumin was loaded into a first glass cartridge; and a wash buffer containing 2.5 mL 25 mM sodium phosphate, pH 5.5 was loaded into a second glass cartridge.

The human serum albumin solution was prepared by dissolving human serum albumin (HSA available from Sigma Chemical Co., St. Louis, Mo.) in 25 mM sodium phosphate buffer, pH 5.5 to a concentration of 8.45 mg/mL.

The first and second cartridges were inserted into one dual barrel syringe housing. A third cartridge and fourth cartridge were inserted into another dual barrel syringe housing attached to the other end of the glass column. The third and fourth cartridges were empty when inserted into the housing.

The single-pass run was performed in the same manner as the single-pass run of Example 1. Thus, all of the unbound HSA was collected in the third cartridge.

The multi-pass run was performed in the same manner as the multi-pass run of Example 1. Thus, all of the unbound HSA was collected in the third cartridge.

Approximately 4.3 mL of treated solution was collected in each run. The amount of HSA loaded into each first cartridge and collected in each third cartridge was determined using the biocinchoninic acid (BCA) protein assay (available from Pierce, Rockford, Ill.). Approximately 16.9 mg HSA was loaded into each first cartridge. 3.6 mg of unbound HSA was measured in the collected solution in the single-pass run, indicating that approximately 13.3 mg of HSA was bound to the column in the single-pass run. 3.3 mg of HSA remained unbound in the multi-pass run, indicating that approximately 13.6 mg of HSA was bound to the column in the multi-pass run.

Example 3

Hydrophobic Immobilization and Elution

A hydrophobic immobilization system was constructed and used for each of two runs, a single-pass run and a multi-pass run. The system was constructed as described in Example 1, with the following exceptions: the glass column was packed with dodecyl agarose (available from Sigma, St. Louis, Mo.) and was equilibrated with phosphate buffered saline (PBS), pH 7.2; a peptide solution was loaded into the first cartridge; and a wash buffer containing 2.5 mL PBS at pH 7.2 was loaded into a second cartridge.

The peptide solution was prepared by proteolyzing bovine serum albumin (BSA available from Sigma, St. Louis, Mo.) that had been dissolved in PBS, pH 7.2. Proteolysis was conducted by adding 1.6 mg TCPK trypsin (available from Pierce, Rockford, Ill.) that was freshly dissolved in water. The proteolysis solution was allowed to incubate for 72 hours at 37° C. The resulting peptide solution contained peptides at a concentration of 304 mg/mL, based upon spectrophotometric analysis at 214 nm.

The first and second cartridges were inserted into one dual barrel syringe housing. A third cartridge and fourth cartridge were inserted into another dual barrel syringe housing attached to the other end of the glass column. The third and fourth cartridges were empty when inserted into the housing.

The single-pass run was performed in the same manner as the single-pass run of Example 1. Thus all unbound peptide was collected in the third cartridge.

The multi-pass was performed in the same manner as the multi-pass run of Example 1. Thus, all unbound peptide was collected in the third cartridge.

Approximately 3.5 mL of solution was collected in each run. The amount of BSA peptides in the original sample solution and each collected solution was determined by spectrophotometric analysis at 214 nm. The starting solution in each run contained approximately 456 mg (1.5 mL) of BSA peptides. 240 mg of unbound peptides were collected in the flow-through of the single-pass run, indicating that 216 mg of BSA peptides were immobilized by the column. 247 mg of unbound peptides were collected in the flow-through of the multi-pass run, indicating that 209 mg of BSA peptides were immobilized in the multi-pass experiment. Thus, there was no discernable increase in hydrophobic immobilization of BSA peptides by increasing the number of passes through the dodecyl agarose column.

Next, the immobilized peptides were eluted from each of the single-pass run column and the multi-pass run column. For each elution, the first and second cartridges were replaced in one syringe housing with cartridges containing 2.5 mL of 70/30 acetonitrile/water (v/v) containing 0.1% trifluoroacetic acid as an elution buffer. Also, the third and fourth cartridges were replaced with empty collection cartridges in the other dual barrel syringe housing.

Each elution was performed in the same manner as the single-pass run of Example 1. Thus, in each elution, protein eluted from the column was collected in the third cartridge.

The volume of collected eluate was 4.7 mL for each elution. The amount of eluted BSA peptide collected in the third cartridge of each elution was determined by measuring the absorbance at 214 nm. The mass of BSA peptides eluted from the single-pass run was 110 mg (of the 216 mg hydrophobically bound to the column in a single pass. The mass of BSA peptides eluted from the multi-pass run was 128 mg (of the 209 mg of BSA peptides immobilized to the column in he multi-pass run).

Example 4

Size Exclusion Separation

A size exclusion separation system was constructed as described in Example 1, with the following exceptions: the glass column was packed with Sephadex G-25 (available from Amersham Pharmacia Biotech AB, Uppsala, Sweden) and was equilibrated with phosphate buffered saline (PBS), pH 7.2; 200 µL of a dye-labeled protein solution was loaded into a first glass cartridge; and a wash buffer containing 2.5 mL PBS buffer solution at pH 7.2 was loaded into a second glass cartridge.

The dye-labeled protein solution was prepared by dissolving 4 mg of rhodamine-labeled BSA (Albumin, bovine-sulforhodamine 101 acid chloride, available from Sigma, St. Louis, Mo.) in 200 µL PBS, pH 7.2.

The first and second cartridges were inserted into one dual barrel syringe housing. A third cartridge and fourth cartridge were inserted into another dual barrel syringe housing attached to the other end of the glass column. The third and fourth cartridges were empty when inserted into the housing.

The plunger rods of the second and fourth cartridges were immobilized, but the plunger rod of the third cartridge was not immobilized. Positive pressure was applied to the plunger rod of the first cartridge, thereby causing the dye-labeled protein solution to flow into the bead-packed column at a rate of 0.5 mL/min. The labeled BSA solution formed a purple layer on the bead bed.

The plunger rod of the first cartridge was immobilized and the plunger rod of the second cartridge was released from immobilization. Positive pressure was applied to the plunger rod of the second cartridge, thereby causing wash solution to flow into the column at a rate of 0.1 mL/min.

Separation of the rhodamine-labeled BSA from unreacted rhodamine was observable on the column during the flow through. The dye-protein fraction was contained in a first clearly delineated band. Unreacted dye molecules were contained in a trailing clearly delineated band. Thus, the dye-protein band was collected in the third cartridge. When the entire dye-protein band had been collected, the plunger rod of the third cartridge was immobilized and the plunger rod of the fourth cartridge was released from immobilization. As positive pressure continued to be applied to the plunger rod of the second cartridge, the unreacted dye band was collected in the fourth cartridge.

Example 5

Cartridge Chemical Reaction

This example demonstrates the utility of the multiple cartridge design for conducting chemical reactions. A system similar to that described in Example 1 was employed, with the following exceptions: the glass column was replaced with plastic tubing filled with 0.2 M sodium carbonate buffer, pH 9.97; the first cartridge was loaded with 3.2 mg BSA solid; the second cartridge was loaded with FLORORLINK (Amersham Pharamcia Biotech) Cy5 non-functional dye solid; and the third cartridge was loaded with 1.5 mL of 0.2M sodium carbonate buffer, pH 9.97.

Cy5 is a fluorescent dye that contains a functional group that can covalently attach the dye to a protein such as BSA.

The first and second cartridges were inserted into one of the dual barrel syringe housings. The third cartridge and a fourth cartridge were inserted into the other syringe housing. The third and fourth cartridges were empty when inserted into the housing.

The plungers of second and fourth cartridges were immobilized. The plunger of first cartridge was not immobilized. Positive pressure was applied to the plunger of the third cartridge, thereby forcing sodium carbonate buffer that was loaded in the plastic tubing into the first cartridge, which contained the BSA solid. The BSA dissolved in the buffer solution entering the first cartridge, thereby forming a BSA solution.

The plungers of the third and fourth cartridges were immobilized and the plunger of second cartridge was released from immobilization. Positive pressure was applied to the plunger of the first cartridge, thereby transferring the BSA solution to the second cartridge. The FLORORLINK Cy5 dye was immediately solubilized by the BSA solution and the solution turned deep blue. The flow was reversed to further mix the reaction solution. The solution was allowed to react for 20 minutes, thereby generating dye-labeled BSA.

Dye-labeled BSA was purified by separation using Sephadex G-25 (PD-10 column available from Amersham Pharmacia Biotech AB, Uppsala, Sweden). A well-defined separation between the dye-labeled BSA and the unreacted dye was observed on the column while eluting with water.

Example 6

Immobilized Chemical Reaction

This example demonstrates the enhancement of a chemical reaction on an immobilized matrix when the analyte is passed through an immobilized matrix multiple times. In this example, a protein solution was passed through a matrix containing immobilized trypsin. The trypsin cleaves the protein in the solution, thereby generating peptide fragments.

An immobilized chemical reaction system was constructed and used for each of two runs, a single-pass run and a multi-pass run. The system was similar to that described in Example 1, with the following exceptions: the glass column was packed with trypsin (TPCK treated) immobilized on beaded agarose (available from Sigma, St. Louis, Mo.) and was equilibrated with 100 mM Tris, pH 8.2; 1 mL of a BSA solution was loaded into a first glass cartridge; and 2.5 mL 100 mM Tris, pH 8.2 was loaded into a second glass cartridge.

The BSA solution was prepared by dissolving bovine serum albumin (BSA available from Sigma Chemical Co., St. Louis, Mo.) in 100 mM Tris, pH 8.2 to an approximate concentration of 5 mg/mL.

The first and second cartridges were inserted into one dual barrel syringe housing. A third cartridge and fourth cartridge were inserted into another dual barrel syringe housing attached to the other end of the glass column. The third and fourth cartridges were empty when inserted into the housing.

In the single-pass run, the BSA solution was introduced into the bead-packed column from the first cartridge by manipulation of the plunger rods as previously described. However, the BSA protein solution was allowed to react with the immobilized trypsin beads for 65 minutes at 23° C. After 65 minutes the column containing the BSA protein/peptide solution was washed with the buffer solution from the second cartridge. The wash was performed as previously described. Thus, all of the trypsinized BSA solution was collected in the third cartridge.

In the multi-pass run, the BSA solution was passed back and forth through the bead-packed column 31 times at a rate of approximately 0.5 mL/min. The column was maintained at a temperature of 23° C. during the 31 passes. After the 31 passes, all of the trypsinized BSA solution was collected in the third cartridge.

Approximately 3.5 mL of trypsinized BSA solution was collected in each run. Analysis of the extent of proteolysis was accomplished using size exclusion chromatography (SEC). Due to the lack of a chromophore in the sample, fractionation of protein and unreacted dye fractions using SEC were accomplished by analogy to the following standard.

In order to approximate the BSA solutions collected in the single-pass run and the multi-pass run, above, but have a chromophore present, a solution of dye-labeled BSA was prepared. It was assumed that all of the BSA from the original sample solution (5 mg) was collected in the collected solutions (3.5 mL) of each run. Thus, 5 mg of dye-labeled BSA (albumin, bovine-sulforhodamine 101 acid chloride, Sigma, St. Louis, Mo.) was dissolved in 3.5 mL 100 mM Tris, pH 8.2. The resulting dye-labeled BSA standard solution approximated the SEC characteristics of the solutions collected in the single-pass run and the multi-pass run.

The rhodamine-labeled BSA solution was applied to a Sephadex G-25 column (PD-10 column; Amersham Pharmacia Biotech AB, Uppsala, Sweden). A well-defined separation between the rhodamine-labeled BSA and unreacted dye was observed on the column while eluting with 100 mM Tris, pH 8.2. The leading band contained rhodamine-labeled BSA and was collected in a volume of 7 mL. Elution of the unreacted dye required a collection volume of 20 mL.

Based on this standard, the solutions collected in the single-pass run and the multi-pass run were individually separated using SEC. For each separation, a 7 mL fraction (the non-proteolyzed protein fraction) and a 20 mL fraction (the proteolyzed peptide fraction) were collected.

The four fractions (the single-pass protein fraction and peptide fraction, and the multi-pass protein fraction and peptide fraction) were subjected to one-dimensional gel electrophoresis and stained with Coomasie blue. A stained band appeared at approximately 68 kDa, corresponding to non-proteolyzed BSA, for the protein fractions and was absent for the peptide fractions, confirming that any non-proteolyzed BSA was limited to the protein fraction.

Matrix Assisted Laser Desorption Ionization—Time of Flight Mass Spectrometry (MALDI-TOFMS) was conducted (Voyager, Applied Biosystems, Foster City, Calif.) on each of the solutions to determine the extent of trypsin proteolysis of the four samples. Samples were analyzed on a gold matrix by spotting 2 $\mu$L of each fraction, followed by 1 $\mu$L of matrix solution (alpha-cyano 4-hydroxycinnamic acid in acetonitrile:water, 1:1 with 1% trifluoroacetic acid) and analyzing the sample according to the manufacturer's instructions.

The analysis showed that more complete proteolysis of the BSA occurred in the multi-pass run than in the single-pass run. The BSA molecular ion peak (~67 kDa) obtained from the single-pass experiment was approximately twice the intensity as the molecular ion peak obtained from the multi-pass experiment, indicating that more BSA was proteolyzed in the latter experiment.

Example 7

Affinity Immobilization of Two Components from One Sample

This example demonstrates the simultaneous removal of two human proteins, albumin and IgG, from human serum using a single column containing a mixture of immobilized affinity reagents. The system was constructed as described in Example 2, with the following exceptions: the glass column was packed with a mixture of 600 $\mu$L Mimetic Blue SA P6XL beads and 400 $\mu$L Mabsorbent A2P beads (both available from ProMetic BioSciences Ltd., Isle of Man, British Isles) and was equilibrated with 50 mM sodium phosphate buffer, pH 6.0 containing 0.9% NaCl; 1.0 mL of a human serum sample was loaded into a first glass cartridge; 2.5 mL and 1.5 mL of a 50 mM sodium phosphate buffer, pH 6.0 were loaded into a second and third cartridge respectively.

The human serum sample was prepared by centrifuging 1.0 mL of human serum (Impath Predictive Oncology, Franklin, Mass.) in a microfuge tube for 10 minutes at 6,000 rpm in a tabletop centrifuge (VWR Scientific, West Chester, Pa.). 200 $\mu$L of the supernatant was diluted with 1.8 mL of 50 mM sodium phosphate buffer, pH 6.0 containing 0.9% NaCl in order to form the human serum sample that was loaded into the first cartridge.

The first and second cartridges were inserted into one dual barrel syringe housing. The third and a fourth cartridge were inserted into another dual barrel syringe housing attached to the other end of the glass column. The fourth cartridge was empty when inserted into the housing.

Positive pressure was applied to the plunger rod of the first cartridge, thereby introducing the starting human serum into the glass column and contacting the serum with the mixture of beads containing mixed immobilized affinity agents for albumin and IgG. The plunger rods of the second and third cartridges were immobilized, but the plunger rod in the fourth cartridge was not immobilized. Thus, liquid collected in the fourth cartridge as the plunger of the first cartridge was advanced. When the plunger rod of the first cartridge was fully advanced, all of the starting human serum had been introduced into the column.

Next, the plunger rods of the first and third cartridges were immobilized and the plunger rod of the second cartridge was released from immobilization. Positive pressure was applied to the plunger rod of the second cartridge so that the buffer solution loaded into the second cartridge was introduced into the column, thereby washing the treated serum from the column. Because the plunger rod in the fourth cartridge was not immobilized, treated serum washed from the column was directed towards and collected in the fourth cartridge.

Next, the plunger rods of the second and third cartridge were immobilized and the plunger rod of the first cartridge was released from immobilization. Positive pressure was alternately applied to the plunger rods of the fourth cartridge and first cartridge so that the treated serum was passed back and forth through the bead-packed column eight more times. Whenever positive pressure was being applied to the plunger rod of one of the first or fourth cartridge, the plunger rod of the other cartridge ("the passive cartridge") was allowed to be displaced outward with respect to the cartridge, thereby allowing the treated serum to temporarily collect in the passive cartridge.

After a total of nine passes through the column most of the treated serum had been collected in the fourth cartridge. The plunger rods of the first and fourth cartridges were immobilized and the plunger rods of the second and third cartridges were released from immobilization. Positive pressure was applied to the plunger rod of the third cartridge so that the buffer solution loaded in the third cartridge was then introduced into the column, thereby washing the remaining treated serum from the column. The remaining treated serum and wash buffer were collected in the second cartridge.

Thus, all of the treated serum was collected in the fourth cartridge and the second cartridge. The contents of the second cartridge and the fourth cartridge were combined and the resultant volume of the combined treated serum was 4.5 mL.

A BCA protein assay (Pierce, Rockford, Ill.) was performed on both the starting human serum sample and the treated serum, the combined contents of the third and fourth cartridges. The starting human serum sample contained 7.51 mg of total protein. The treated serum contained 1.26 mg of total protein. Therefore 6.25 mg of protein was retained in the column.

The protein retained in the column was eluted by liquid chromatography (UPC-900, Amersham Pharmacia Biotech, Uppsala, Sweden) using 0.1 M CAPS (3-cyclohexylamino-1-propane sulfonic acid) buffer, pH 11.5. The resulting eluent contained 6.23 mg of total protein according to a BCA protein assay.

Samples of the starting human serum, treated serum and the column eluent were analyzed by one dimensional gel electrophoresis using a 4–15% Tris-HCl Ready Gel (available from BioRad, Hercules, Calif.) in a running buffer of Tris buffer containing glycine and sodium dodecyl sulfate. The gel was also loaded with an HSA standard (Sigma Chemical Co., St. Louis, Mo.) and protein standards (Broadband Standards available from BioRad, Hercules, Calif.). Each sample was denatured by mixing 20 $\mu$L of sample with 40 $\mu$L cracking buffer (50 $\mu$L 2-mercaptoethanol and 950 $\mu$L Laemmli sample buffer (BioRad). 40 $\mu$L of each denatured sample was loaded into the well of a separate lane of the Ready Gel. The gel was run at 120 V for approximately 1 hour.

The resulting gel was stained for 1 hour using BioSafe Coumassie (BioRad) and destained in deionized water overnight. The most-intensely stained proteins in the starting human serum sample and the column eluent were consistent with the molecular weights for HSA, IgG heavy-chain, and IgG light-chain. The lane containing the column eluent also contained additional proteins. However, the intensity of the stain for the additional proteins was much less than the intensity of staining of the HSA, IgG heavy-chain and IgG light-chain. No IgG heavy-chain or IgG light-chain was detected in the lane containing treated serum; a relatively light-intensity band of HSA was detected.

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A device for treating a liquid sample comprising:
   a firm chamber having a variable volume;
   a second chamber having a variable volume;
   a third chamber having a variable volume;
   an interconnect comprising one or more passageways, each passageway engaged with one or more chambers so that the interconnect provides fluid communication between the first chamber, second chamber and third chamber; and
   a treating substance that comprises a functionalized solid support or an affinity reagent included in at least one of the first chamber, the second chamber, the third chamber, or at least one passageway of the interconnect;
   wherein the device is configured so that movement of the liquid sample through the device is controlled by changing the variable volumes of two or more chambers.

2. The device of claim 1 further comprising a second treating substance provided in the first chamber, the second chamber, the third chamber or at least a portion of the interconnect.

3. The device of claim 2 wherein the second treating substance comprises a filter, a membrane, a size exclusion medium, a derivalized solid support, a reactant, an affinity reagent, or a buffer.

4. The device or claim 1 wherein the interconnect comprises two more passageways.

5. The device of claim 4 wherein the interconnect further comprises two or more treating substances so that a first treating substance is provided in a first passageway that is different than a second treating substance provided in a second passageway.

6. The device of claim 1 further comprising an actuator connected to at least two chambers and is configured to regulate the variable volumes of the at least two chambers.

7. The device of claim 1 wherein at least one chamber is reversibly removable from the device.

8. The device of claim 1 further comprising at least one detection element for detecting at least a portion of the liquid sample.

9. The device of claim 1 wherein the detection element comprises a pH detector, a spectrophotometric detector, a fluorescence detector, a conductivity detector or a refractive index detector.

10. The device of claim 1 further comprising at least one temperature-regulating element for regulating the temperature of at least a portion of the interconnect or at least a portion of at least one chamber.

11. The device of claim 1 further comprising at least one controllable element connected to at least one controller element.

12. The device of claim 11 wherein the controllable element comprises an actuator for regulating the variable volume of at least one chamber, a detection element, or a temperature-regulating element.

13. The device of claim 11 wherein the controller element comprises a programmable microprocessor.

14. The device of claim 1 further comprising at least one additional chamber having a variable volume that is in fluid communication with at least a portion of the interconnect.

15. A method of treating a liquid sample comprising:
   a) providing an device that comprises:
      i) a first chamber having a variable volume,
      ii) a second chamber having a variable volume,
      iii) a third chamber having a variable volume,
      iv) an interconnect comprising one or more passageways, each passageway engaged with one or more chambers so that the interconnect provides fluid communication between the first chamber, the second chamber and the third chamber, and
      v) a treating substance that comprises a functionalized solid support or an affinity reagent included in at least one of the first chamber, the second chamber, tho third chamber or a portion of the interconnect,
      wherein the device is configured so that movement of the liquid sample through the device is controlled by changing the variable volume of two or more chambers;
   b) providing a liquid sample in the first chamber; and
   c) decreasing the volume of the first chamber and increasing the volume of at least one other chamber, thereby contacting at least at portion of the sample with at least a portion of the treating substance so that the sample is at least partially treated by the treating substance, thereby also directing at least a portion of the sample toward the at least one other chamber.

16. The method of claim 15 wherein the step of decreasing the volume of the first chamber further comprises decreasing the volume of the second chamber.

17. The method of claim 15 wherein a treated portion of the sample is directed into a collection chamber, and the method further comprises the step of removing the collection chamber from the device.

18. The method of claim 15 wherein increasing the volume of at least one other chamber comprises increasing the volume of the second chamber, thereby directing at least a portion of the sample toward the second chamber.

19. The method of claim 18 wherein at least a portion of the sample directed toward the second chamber comprises sample that has been treated by the treating substance.

20. The method of claim 18 wherein the device further comprises a second treating substance included in at least one of the second chamber, the third chamber, or a portion of the interconnect; and the method further comprises the step of decreasing the volume of the second chamber and increasing the volume of the third chamber, thereby directing at least a portion of the at least partially treated sample toward the third chamber and causing the at least partially treated sample to be further at least partially treated by the second treating substance.

21. The method of claim 15 wherein the device further comprises at least one controllable element connected to at least one controller element wherein the controller element comprises a programmable processor, and at least one portion of the method is automated and controlled by the programmable microprocessor.

* * * * *

UNITED STATES PATENT AND TRADEMARK OFFICE
CERTIFICATE OF CORRECTION

PATENT NO.    : 6,820,506 B2
DATED         : November 23, 2004
INVENTOR(S)   : Kipke, Cary A.

It is certified that error appears in the above-identified patent and that said Letters Patent is hereby corrected as shown below:

Column 23,
Line 50, delete "firm" and insert in place thereof -- first --.

Column 24,
Line 7, delete "derivalized" and insert in place thereof -- derivatized --.
Line 9, delete "or" and insert in place thereof -- of --.
Line 10, after "two" insert -- or --.
Line 57, delete "tho" and insert in place thereof -- the --.
Line 60, delete "volume" and insert in place thereof -- volumes --.
Line 65, after "at least" delete "at" and insert in place therof -- a --.

Signed and Sealed this

Nineteenth Day of April, 2005

JON W. DUDAS
*Director of the United States Patent and Trademark Office*